United States Patent [19]

Kankare et al.

[11] Patent Number: 5,202,423
[45] Date of Patent: Apr. 13, 1993

[54] TERPYRIDINE DERIVATIVES

[75] Inventors: Jouko Kankare; Harri Takalo; Elina Hänninen; Matti Helenius, all of Turku; Veli-Matti Mukkala, Kaarina, all of Finland

[73] Assignee: Wallac OY

[21] Appl. No.: 687,498

[22] Filed: Apr. 19, 1991

Related U.S. Application Data

[63] Continuation of Ser. No. 466,414, Mar. 5, 1990, abandoned.

[30] Foreign Application Priority Data

Jul. 8, 1988 [SE] Sweden ................................. 8802575

[51] Int. Cl.$^5$ ..................... C07K 15/28; C07K 17/02; A61K 39/44; A61K 49/02
[52] U.S. Cl. ............... 530/391.5; 530/391.3; 530/402; 530/404; 530/405; 530/406; 530/408; 530/409; 530/410; 436/546; 436/545; 436/544; 536/24.3; 536/24.31; 536/24.32; 534/15; 544/333; 546/23; 546/176; 546/256
[58] Field of Search ............... 530/402, 403, 404, 405, 530/406, 408, 409, 410, 388, 389, 390, 391, 391.3, 391.5; 436/546, 545, 544; 544/333; 546/23, 176, 256; 534/15; 536/27

[56] References Cited

U.S. PATENT DOCUMENTS

| | | | |
|---|---|---|---|
| 4,637,988 | 1/1987 | Hinshaw et al. | 436/546 |
| 4,784,912 | 11/1988 | Schaeffer et al. | 428/402 |
| 4,801,504 | 1/1989 | Burdick et al. | 436/529 |
| 4,837,169 | 6/1989 | Toner | 436/546 |
| 4,859,777 | 8/1989 | Toner | 546/256 |

FOREIGN PATENT DOCUMENTS 0195413 9/1986 European Pat. Off. .
0203047 11/1986 European Pat. Off. .

OTHER PUBLICATIONS

CA98(13):107123t Constable et al. Polyhedron 1(3):303-6, 1982.
Mears et al. (1984) Anal. Biochem. 142;68-78.

Primary Examiner—Christine M. Nucker
Assistant Examiner—Kay Kim
Attorney, Agent, or Firm—Fred Philpitt

[57] ABSTRACT

The invention pertains to terpyridine compounds having structure (I). These compounds form fluorescent lanthanide chelates with the appropriate metal ions. The fluorescent metal chelates are useful as probes in time-resolved fluorescence spectroscopy.

7 Claims, No Drawings

TERPYRIDINE DERIVATIVES

This is a continuation of application Ser. No. 466,414, filed Mar. 5, 1990 now abandoned, and the benefits of 35 USC 120 are claimed relative to it.

FIELD OF INVENTION

The invention pertains to organic complexing agents (ligands or chelators) having a 2,2':6',2" terpyridine structure. Throughout this specification compounds having this structure will be called terpyridines, if not otherwise specified. The ligands of the invention form fluorescent lanthanide chelates with the appropriate metal ions.

The new chelates as well as the ligand as such may find application in those fields that are classical for chelates. The fluorescent metal chelates of our invention are useful as probes in time-resolved fluorescence spectroscopy. Contrary to many other known lanthanide chelators, the chelators of this invention very often give strongly fluorescent chelates with both $Tb^{3+}$ and $Eu^{3+}$. This might imply that they will be very important in multi labeling techniques.

The sensitivity of the analytical methods based on molecular fluorescence is limited by the background signal due to either Raman scattering or fluorescent impurities in the sample. Both of these interferences are generally short-lived phenomena, i.e. the radiative transition following the excitation of the molecule occurs within a microsecond time span. Thus any compound with a long-lived fluorescence can be effectively determined in the presence of short-lived background if a fluorometer with time resolution is at hand. In this fluorometer the sample is illuminated by an intermittent light source such that the long-lived fluorescence is measurable during the dark period subsequent to the decay of the short-lived background.

DESCRIPTION OF THE PRIOR ART

The chelating ability of terpyridines, bipyridines and substituted pyridines are well known EP-A-68,875 (p. 29), Chemical Abstracts 98 (1983) 226913k, 102 (1985) 71589j, 103 (1985) 71419z and 106 (1987) 94885, FR-A-2,570,703, Chem Berichte 118 (1985) 212-7, EP-A-195,413 and EP-A-203,047).

Time resolved fluorescence spectroscopy by the use of fluorescent lanthanide chelates has also been known for some time. The methods presented in DE-A-2,628,158 and U.S. Pat. No. 4,374,120 make use of beta-diketones as ligands in fluorescent lanthanide chelates used in fluoroimmunoassays. In DE-A-2,628,158 the light absorbing moiety of the fluorescent chelate is covalently conjugated to an antigen or antibody which during the test procedure is allowed to form an immune complex with its immunological counterpart. In this type of assays the test protocol is arranged so that the amount of the immune complex formed will constitute indication means for the substance that is to be detected (=analyte). The lanthanide chelate-labeled immune reactant used has an epitope in common with the analyte (analyte analogue) or is an antibody active component directed against the analyte or against other antigenic or haptenic material used for the formation of the immune complex. In many versions of this type of assays the chelate may be conjugated directly to a molecule employed as an antigen or hapten. There are several different ways of categorizing fluoroimmunoassays and other assays employing biospecific affinity reactions (reactants). If, before the fluorescence measurement, the chelate incorporated in the immune complex is separated from the portion of the chelate that is not incorporated, the methods are called heterogenous. If no such separation step is included they are called homogenous. These two variants put different demands on the lanthanide chelate used. The homogenous ones require that the chelate changes its fluorescent properties in a measurable manner as a consequence of the immune complex formation, while no such requirement is needed for the heterogenous versions. Immunoassays are just one example of methods that utilize biospecific affinity reactions. Analogously there are assay systems utilizing other types of biospecific affinity such as between DNA—complementary DNA, Protein A—Fc-part of IgG, lectin—carbohydrate structure etc. The principles and classification outlined above apply equally well to them.

The major short-coming of the fluorescent lanthanide chelates is that they rarely combine good aqueous stability with efficient fluorescence. In aqueous solvents their fluorescence is often quenched by water.

In EP-A-64,484 a version of a lanthanide chelate heterogenous fluoroimmunoassay is given that has no requirements for labels that are good fluorescers. Instead the interest is focused on the aqueous stability of the lanthanide chelate used. The ligand only serves to carry the lanthanide through the separation step, after which the lanthanide cat-ion is dissociated at a low pH and a highly fluorescent chelate is formed with an aromatic beta-diketone as ligand in a micellar phase. This method gives a very good sensitivity but suffers from a somewhat lengthy procedure.

It would be very advantageous to have highly fluorescent lanthanide probes with good aqueous stability. Such probes would allow homogenous assays and shorter assay procedures in heterogenous assays. They would also find use in other fluorescence methods, e.g. fluorescence microscopy.

Lanthanide chelates fluorescing in aqueous media have previously been suggested (EP-A-180,492 (macropolycyclic), EP-A-68,875 (phenols and aryl ethers and one specific terpyridine chelator), EP-A-195,413 (aryl pyridines) and EP-A-203,047 (ethynyl pyridines)). Although they to some degree can compensate for the short-comings set forth above only lanthanide chelates of the ethynyl pyridines (EP-A-203,047)have turned out to exhibit an efficient quantum yield and an aqueous stability for the commercialisation as directly fluorescing labels.

THE INVENTION

The compounds of the invention have the common structure given in formula I and comprise also ordinary analogues thereof, such as acid, ester, salt and chelate forms involving one or more of their chelating heteroatoms.

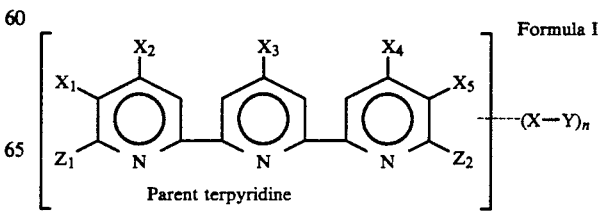

Formula I

Parent terpyridine

In formula I, n is an integer 0, 1, or 2, preferably 1, and specifies that the group X-Y is a substituent replacing a hydrogen or a group $X_1$-$X_5$ in the parent terpyridine compound.

$X_1$-$X_5$ are selected from a) hydrogen b) hydrocarbon group which may be straight, branched or cyclic, such as alkyl, alkenyl, alkynyl and an aromatic group (aryl), and containing additional structures not participating in the chelation such as aromatic ring systems, ether, thioether, ester, amido, amino (primary, secondary or tertiary), carboxy, halo, cyano etc., and other structures exhibiting heteroatoms, c) cyano, halo and nitro, and d) carboxylic acid (COOH), amido ($CONH_2$), amino ($NH_2$), hydroxy (OH), mercapto (SH) and substituted forms of these groups in which hydrogen has been replaced with a hydrocarbon group as defined in b) above, and the hydrogen of the amino and hydroxy group optionally also having the possibility of being replaced with an acyl group, RCO, in which R is an hydrocarbon group as defined in b) above.

Examples of alkyl are lower alkyl having less than 12, such as 1-5, carbon atoms.

Examples of different aromatic groups are phenyl, quinolyl, naphthyl, pyridyl, pyrimidyl etc. all of which may contain additional substituents. By selecting alkenyl, alkynyl or aromatic system directly bound or bound via a carbonyl, or via an uncharged nitrogen atom to anyone of the heteroaromatic rings in formula I, the conjugated electron system can be extended to more aromatic rings or carbon atoms. Preferably at most two aromatic ring structures are conjugated to the terpyridine structure.

The preferred $X_1$-$X_5$ are hydrogen, hydroxyl, alkoxyl, amino, amido, alkyl, such as aminoalkyl, alkylthio, alkylamino, alkynyl, such as aminoethynyl, aryl, such as aminoaryl, aralkyl, aryloxyl, arylamino and arylethynyl, Fenyl(ene) is the preferred aryl moiety. From the synthetic point of view both $X_1$ and $X_5$ are preferably hydrogen.

$Z_1$ and $Z_2$ are chelating groups, that may be identical or different. Preferably $Z_1$ and $Z_2$ are —$CH_2$—Z' and —$CH_2$—Z", respectively, having the chelating ability confined to Z' and Z".

Each of $Z_1$ and $Z_2$ comprises two or more heteroatoms having a free pair of electrons and placed at a distance of two or three atoms from each other. Examples of efficient chelating heteroatoms are amino nitrogen atoms (primary, secondary and tertiary amines), negatively charged oxygen atoms e.g. in carboxylate anions ($COO^-$), enolate anions (C=C—$O^-$)phosphates or phosphonates. Another good chelating structure is the hydroxamate group (CONOH). In most cases the bridge between two neighbouring chelating heteroatoms contains 1, 2 or 3 aliphatic carbon atoms. Among particularly important Z' and Z" structures may be mentioned N-biscarboxymethyl amino and N-biscarboxyethyl amino groups, the analogous phosphate (—N(—$CH_2$—O—$PO_3^{2-}$)$_2$) and phosphonate (—N(—$CH_2$—$PO_3^{2-}$)$_2$) and 2,6dicarboxypiperidin-1-yl. Alternatively, $Z_1$ and $Z_2$ may form a bridge connecting the two outer pyridine rings giving a macrocyclic chelating compound. Preferably such a bridge is —$CH_2$N(CH$_2COO^-$)$CH_2$—(Z'=Z"=$NCH_2COO^-$).

In some compounds of the invention the chelating heteroatoms (N and O) may exist as the corresponding protonated forms and for O also as ester forms, such as lower alkyl ($C_1$-$C_6$) or benzyl esters.

From the spectrofluorometric point of view Z and Z' are preferably chelating to $Eu^{3+}$, $Tb^{3+}$, $Dy^{3+}$ or $Sm^{3+}$.

X-Y represents an inert organic group in which X is an inert and stable bridge and Y is (a) a functional group or (b) a residue of an organic compound (Y') that has properties retained in the compound of formula I (n=1 or 2) after it has been coupled covalently to the parent compound. The term "inert" above means that the group or bridge characterized by this adjective does not have any efficient chelating heteroatom closer than at a distance of four atoms from the heteroatoms participating in the chelation of a joint metal ion. In actual practice this means that the four atoms are normally represented by a four-carbon chain. By "stable" is meant that the bridge X does not deteriorate when the compounds of the invention are used, for instance the bridge does not easily undergo hydrolysis. In formula I, X-Y exist as a substituent replacing a hydrogen in a $Z_1$ and/or $Z_2$ group, preferably in a Z' and/or Z" group, or a hydrogen in one or two $X_1$-$X_5$.

X may contain at least one structural element selected from among the following: —NR— (secondary and tertiary amine), —CONR— and —NRCO— (substituted amide), —S—S— (aliphatic disulfide), —S— (aliphatic thioether), —O— (ether), —COO— and —OOC— (ester), —N=N— (diaza) and pure hydrocarbon chain which may be straight, branched or cyclic and contain from 1 to 12 carbon atoms. The carbon chain may be purely aliphatic or purely aromatic (including phenyl, naphthyl, quinolyl, pyridyl and bipyridyl), and other inert functional groups not participating in the chelation mentioned above. The symbol R in the substituted amide above represents preferably hydrogen but may be alkyl, for instance an alkyl having less than 5 carbon atoms.

Y may be selected from two main categories (A and B below):

A) Y may be the residue of an organic compound (Y') having certain properties which are substantially retained in the compound of formula I (n=1 or 2). The compound (Y') may be a biologically active molecule having the ability to participate in biospecific affinity reactions, such as between antigens (haptens) and the homologous antibody active components, nucleotides, aligonucleotides, complementary nucleic acids (RNA, DNA), lectins and carbohydrate structures, protein A and IgG etc. This type of biologically active molecules are often called targeting substances (targeting molecules). Usually they have been or can be easily derivatized to contain functional groups permitting conjugation to diversified types of compounds. The compound (Y') may also be a multifunctional organic compound being bound by one of its functional groups to the bridge X so as to leave at least one of its remaining functional groups free for further derivatization.

B) Y may be a functional group so selected that it can be made to react chemically with a functional group A of an organic compound (Y') so as to form a covalent linkage between Y' and a compound of formula I (n=1 or 2). The selection of Y deepens on A and vice versa, but it is believed that any artisan can make the proper selection of mutually reactive groups. Y and A may be selected from among electrophilic and nucleophilic groups. If they are a pair of electrophilic groups or a pair of nucleophilic groups, it is possible for instance to (a) employ oxidative coupling for forming the bond (e.g. —SH+HS——S—S—) or (b) convert one of the groups of the pair chemically to a group of the opposite type. An example of the latter case is the activation with bifunctional coupling reagents (also called activation reagents). If Y is nucleophilic and A electrophilic or vice versa these two groups can usually be reacted with each other without any preceding activation. Most nucleophilic groups comprise a heteroatom having an electron pair available for reaction with an electron deficient atom (electrophilic group).

Examples of suitable functional groups include isothiocyanato, bromoacetamido, iodoacetamido, succinamido, pyridyldithio, mercapto, cargoxyl and its active esters (e.g. N-hydroxysuccinimido or p-nitrophenyl), hydroxyl, aldehyde, amino, diazonium, tosyl, mesytylyl, trexyl, phosphodiester or phosphotriester. Other functional groups are known to those skilled in the art.

In a compound according to the invention it is imperative that all the groups mentioned can coexist. However, the reactive group Y does not necessarily have to coexist with a chelating group of the invention. For some purposes the chelating part of the molecule may be temporarily protected e.g. in the form of an ester so that the protected ligand will be coupled to the target molecule, and after deblocking may finally form the desired labelled product. The protective group is chosen in accordance with known principles (see for instance Protective Groups in Organic Synthesis; Greene, Tenn.; John Wiley & Sons Inc; USA (1981). Factors to be taken into account when the group is chosen are inter alia the stability of the compound with which Y is to be reacted, the reactivity of Y and the type of structure formed upon reaction of Y and the compound intended.

The examples of this specification given wellknown methods for introducing functionalized methylene groups next to a pyridine nucleus. These groups can subsequently be reacted with iminobisacetic esters to the formation of chelating groups $Z_1$ and $Z_2$. Phosphonate groups can be introduced according to J. Org. Chem. 31 (1966) 1603— and phosphate groups according to Helv. Chim. Acta 70 (1987) 175. For the formation of chelates with different metal ions, see Nucl. Med. Biol. 13 (1986) 311— and references cited therein. Prior to the first filing of this patent application no publication had presented any good method for the synthesis of iminobisacetic esters derivatives having a functionalized substituent at the methylene group of their acetyl moiety. A synthetic route has been developed at Wallac Oy, Finland and it will be exemplified in this specification in detail (examples 37-45. The so synthesized derivatives may be reacted with 6,6″-bishalomethyl terpyridines analogously to the method given in examples 34-35 below.

The preferred compounds of the invention have been summarized in formula II.

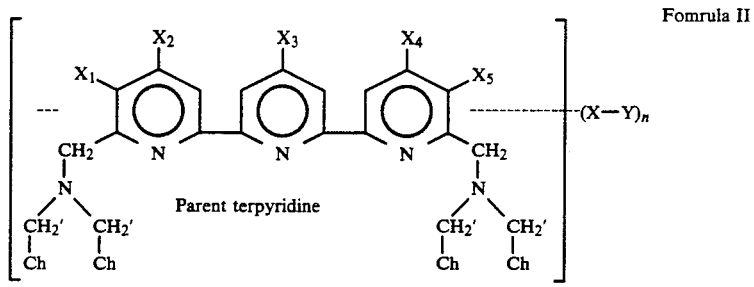

Fomrula II

In formula II, $X_1$-$X_5$, n, X and Y have the same meaning as stated before, except that at most two of $X_1$-$X_5$ are groups other than hydrogen.

-------- means that X-Y is a substituent replacing a group $X_1$-$X_5$ or H'. Ch is a chelating group selected from —COO⁻, —OPO$_3^{2-}$, and —PO$_3^{2-}$. This preferred aspect of the invention also comprises the acid, ester, salt and chelate forms as defined above.

In general terms one mode of our invention is to apply our new fluorescing chelates as probes in time-resolved fluorescent spectrometry. In one aspect the chelating light-absorbing moiety of the chelate is used as a fluorescence enhancer for methods in which substantially non-fluorescent Eu$^{3+}$—, Dy$^{3+}$—, Sm$^{3+}$— or Tb$^{3+}$— chelates are used. See for instance EP-A-64,484 (Wallac Oy) and U.S. Pat. No. 4,352,751 (Wieder). Another aspect is a time-resolved fluorometric method using a fluorescing lanthanide chelate as the probe for the determination of a target substance (structure). Generally these assay methods comprise two steps (i) marking specifically the target structure with a lanthanide (probe) chelate of this invention (or just the chelating ligand if the target is a lanthanide ion forming a fluorescing chelate with the ligant), and (ii) measuring by methods known per se the fluorescence related to said probe. Assay systems employing biospecific affinity reactions as given in the introductory part are one of the most important systems falling under this definition. Accordingly other steps may also be included and be performed before, between or after steps (i) and (ii). Compare also U.S. Pat. No. 4,058,732 (Wieder).

The invention is defined in the appended claims which are part of the description. The invention will now be illustrated with the synthesis of several compounds of the invention.

The structures and the synthetic routes employed in the experimental part are shown in reaction schemes 1-3. Schemes 1 and 2 illustrate terpyridine compounds having a 4′-respective 4- and 4″-substitutent(s). By the proper selection of R¹ in the starting compounds substituents will be introduced permitting either direct coupling or coupling by the use of common bifunctional coupling reagents to a biological active molecule participating in biospecific affinity reactions. Examples of such groups are nucleophilic groups (primary amino, isothiocyanato etc). Scheme 3 illustrates the synthesis of iminobisacetic acid derivatives that can be used for the formation of the chelating groups $Z_1$ and $Z_2$ (of formula I). The derivatives contain a reactive group that cannot participate in the chelating but that can be used to link covalently a biological active molecule of the type as set forth above to the terpyridine structure.

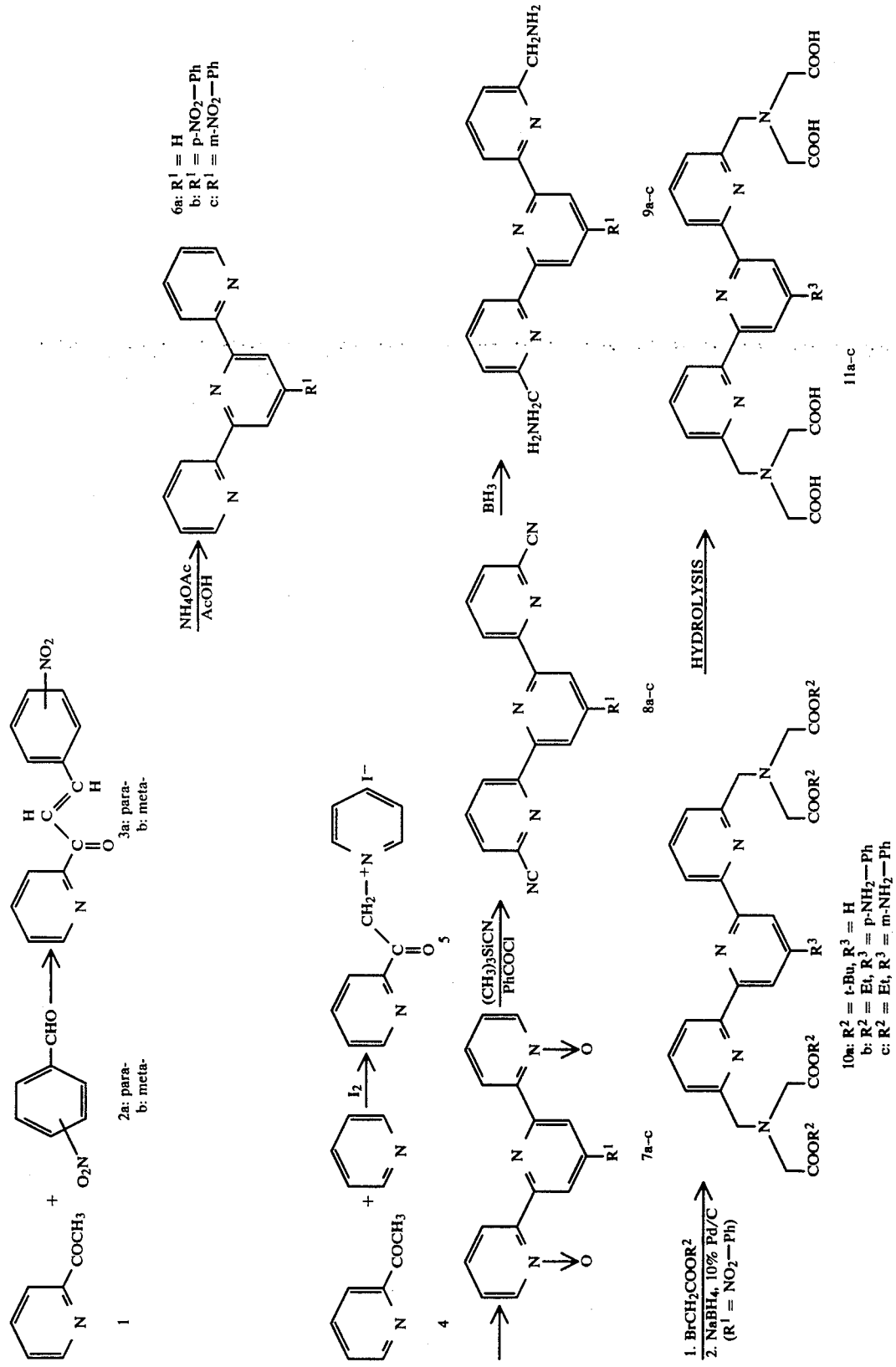

SCHEME 2
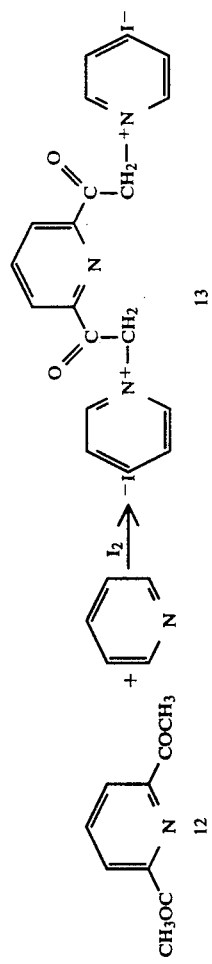
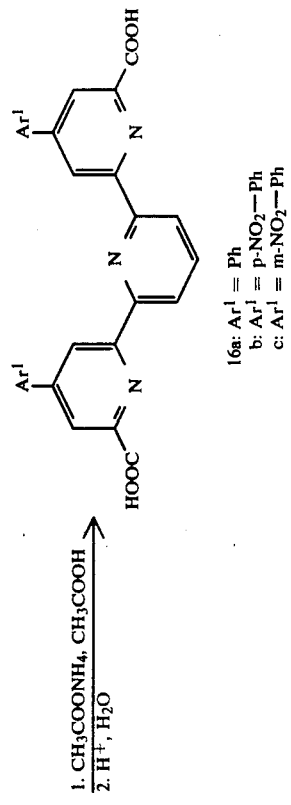
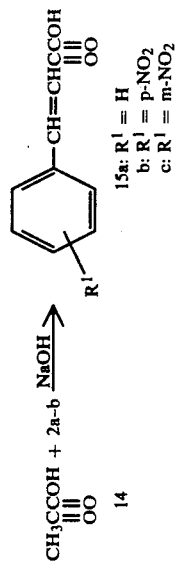
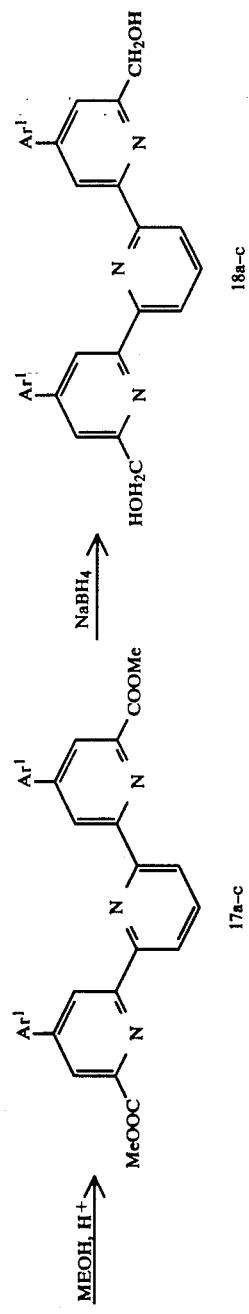

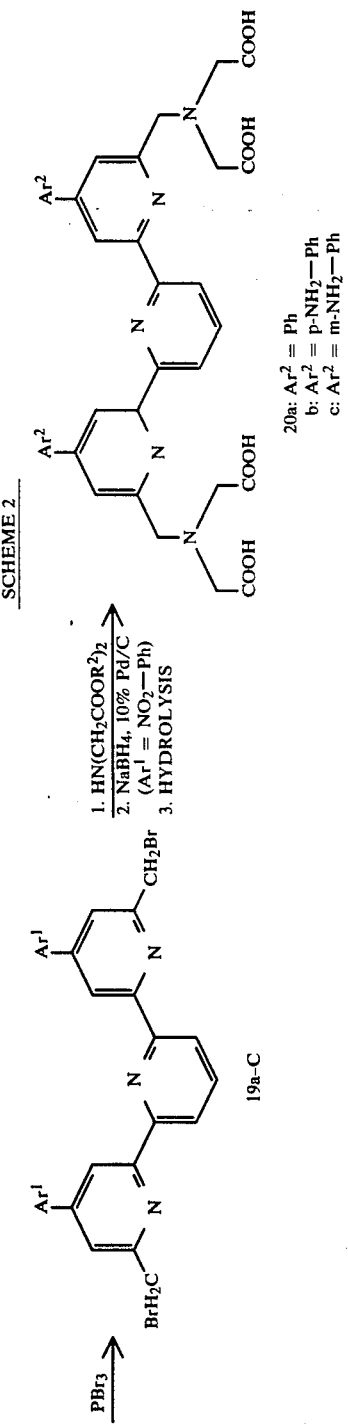

SCHEME 3

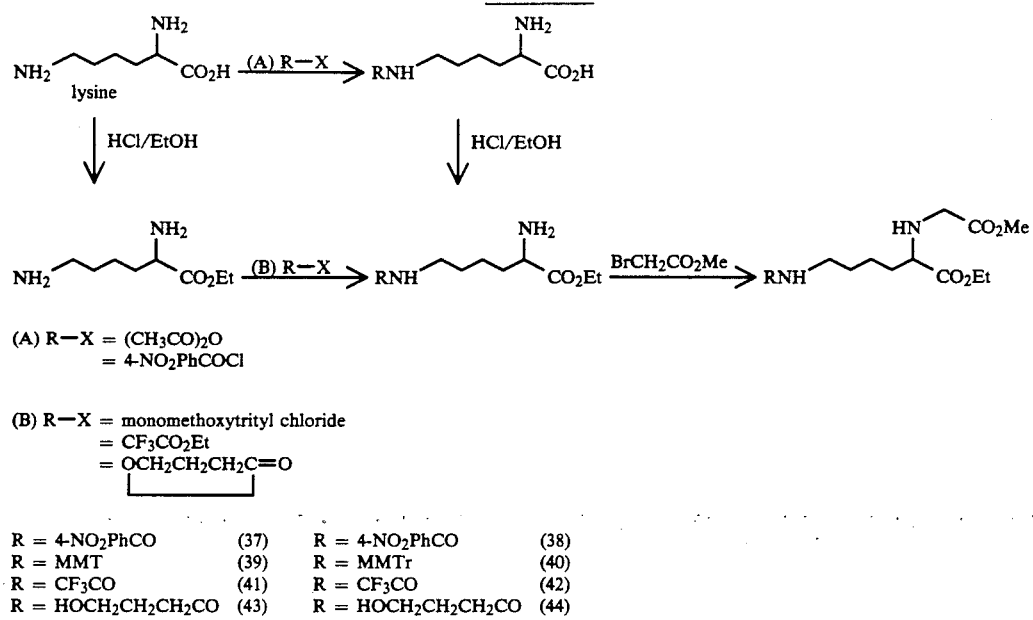

(A) R—X = (CH₃CO)₂O
       = 4-NO₂PhCOCl (B) R—X = monomethoxytrityl chloride
       = CF₃CO₂Et
       = OCH₂CH₂CH₂C=O
         └─────────────┘

R = 4-NO₂PhCO      (37)    R = 4-NO₂PhCO     (38)
R = MMT            (39)    R = MMTr          (40)
R = CF₃CO          (41)    R = CF₃CO         (42)
R = HOCH₂CH₂CH₂CO  (43)    R = HOCH₂CH₂CH₂CO (44)

EXAMPLE 1

1-(2-Pyridyl)-3-(3-nitrophenyl)-2-propenone, 3b

2-Acetylpyridine (1.82 g, 15.0 mmol) and 3-nitrobenzaldehyde (2.27 g, 15.0 mmol) were added to a solution of KOH (0.67 g, 12.0 mmol) in water (6 ml) and methanol (54 ml). The solution was stirred at room temperature for 2 hours, whereafter the precipitation of the product was complete. The precipitate was filtered and washed with methanol.
Yield: 93%
$^1$H NMR (CDCl₃): 7.52–7.55 (1H, m); 7.62 (1H, t, J=8 Hz); 7.91 (1H, dt, J=8 Hz and 2 Hz); 7.94 (1H, d, J=16 Hz); 8.01 (1H, d, j=8 Hz); 8.21 (1H, d, J=8 Hz); 8.26 (1H, dd, J=8 Hz and 2 Hz); 8.44 (1H, d, J=16 Hz); 8.59 (1H, s); 8.78 (1H, d, J=5 Hz).

EXAMPLE 2

1-(2-Pyridyl)-3-(4-nitrophenyl)-2-propenone, 3a

This compound was synthesized using a method analogous to the synthesis described in example 1, 3b. The crude product was crystallized from ethanol.
Yield: 68%
$^1$H NMR (CDCl₃): 7.52–7.56 (1H, m); 7.87 (2H, d, J=9 Hz); 7.91 (1H, dt, J=8 Hz and 2 Hz), 7.92 (1H, d, J=16 Hz); 8.21 (1H, d, J=8 Hz); 8.27 (2H, d, J=9 Hz); 8.43 (1H, d, J=16 Hz); 8.76 (1H, d, J=5 Hz)

EXAMPLE 3

1-(2-Pyridylcarbonylmethyl)pyridinium iodide, 5

2-Acetylpyridine (1.21 g, 10.0 mmol) and iodine (2.54 g, 10.0 mmol) were heated to reflux in pyridine (12 ml) for 1 hour. The solution was cooled, and the dark precipitate was filtered and washed with pyridine.
Yield: 72%
$^1$H NMR (DMSO): 6.51 (2H, s); 7.82–7.85 (1H, m); 8.08 (1H, d, J=7 Hz); 8.14 (1H, dt, J=8 and 2 Hz); 8.28 (2H, t, J=8 Hz); 8.73 (1H, t, J=8 Hz); 8.87 (1H, d, J=5 Hz); 9.00 (2H, d, J=6 Hz).

EXAMPLE 4

4'-(3-Nitrophenyl)-2,2';6',2''-terpyridine, 6c 1-(2-Pyridyl)-3-(3-nitrophenyl)-2-propenone (2.54 g, 10.0 mmol) and 1-(2-pyridylcarbonylmethyl)pyridinium iodide (3.26 g, 10.0 mmol) and ammonium acetate (4.82 g, 60.0 mmol) were heated to reflux in acetic acid (37 mol) for 1.5 hours whereafter the solution was cooled and the precipitate was filtered and washed with acetic acid. The crude product was crystallized from acetonitrile.
Yield: 56%
$^1$H NMR (DMSO): 7.54–7.58 (2H, m); 7.89 (1H, t, J=8 Hz); 8.06 (2H, dt, J=8 Hz and 2 Hz); 8.38–8.41 (1H, m); 8.41–8.44 (1H, m); 8.66 (1H, t, J=2 Hz); 8.70 (2H, d, J=8 Hz); 8.78–7.80 (4H, m).

EXAMPLE 5

4'-(4-Nitrophenyl)-2,2';6',2''-terpyridine, 6b

This compound was synthesized using a method analogous to the synthesis described in example 4, 6c. The crude product was purified with flash chromatography (silica, chloroform with methanol gradient).
Yield: 56%
$^1$H NMR (DMSO): 7.53–7.56 (2H, m); 8.05 (2H, dt, J=8 Hz and 2 Hz); 8.22 (2H, d, J=9 Hz); 8.40 (2H, d, J=9 Hz); 8.68 (2H, d, J=8 Hz); 8.76 (2H, s); 8.77 (2H, d, J=5 Hz).

EXAMPLE 6

2,2';6',2''-Terpyridine-N,N''-dioxide, 7a 2,2';6',2''-Terpyridine (0.94 g, 4.0 mmol) was dissolved in dichloromethane (80 ml) and m-chloroperbenzoic acid (2.60 g, 15.1 mmol) was added. After stirring overnight some dichloromethane was added and the solution was washed with 10% sodium carbonate. The dichloromethane phase was evaporated and purified with flash chromatography (silica, chloroform with methanol gradient).
Yield: 93%

¹H NMR (CDCl₃): 7.31 (2H, dd, J=2 and 7 Hz); 7.40 (2H, dd, J=1 and 8 Hz); 7.98 (1H, t, J=8 Hz); 8.20 (2H, dd, J=2 and 8 Hz); 8.37 (2H, dd, J=1 and 7 Hz); 8.94 (2H, d, J=8 Hz).
UV ($\lambda_{max}$ in ethanol): 241, 279.

EXAMPLE 7

4'-(4-Nitrophenyl)-2,2';6',2''-terpyridine-N,N''-dioxide, 7b

This compound was synthesized using a method analogous to the synthesis described in Example 6, 7a. The crude product was purified by crystallization from a mixture of acetonitrile and methanol.
Yield: 51%
¹H NMR (DMSO): 7.52–7.58 (4H, m); 8.11 (2H, dd, J=7 Hz and 2 Hz); 8.26–8.28 (2 H, m); 8.41–8.46 (4H, m); 9.16 (2H, s).

EXAMPLE 8

4'-(3-Nitrophenyl)-2,2';6',2''-terpyridine-N,N''-dioxide, 7c

This compound was synthesized using a method analogous to the synthesis described in Example 6, 7a. The crude product was purified by crystallization from a mixture of ethanol and chloroform.
Yield: 78%
¹H NMR (DMSO): 7.52–7.58 (4H, m); 7.89 (1H, t, J=8 Hz); 8.25–8.28 (2H, m); 8.31 (1H, d, J=8 Hz); 8.38 (1H, dd, J=8 Hz and 1 Hz); 8.43–8.45 (2H, m); 8.61 (1H, t, J=2 Hz); 9.17 (2H, s).

EXAMPLE 9

6,6''-Dicyano-2,2';6',2''-terpyridine, 8a 2,2';6',2''-Terpyridine-N,N''-dioxide (7a) (0.96 g, 3.6 mmol) was suspended in dichloromethane (10 ml). N,N-dimethylcarbamyl chloride (0.95 g, 8.8 mmol) and trimethylsilyl cyanide (1.26 g, 12.7 mmol) were added. After stirring for two weeks at room temperature, 10% potassium carbonate was added until the solution was neutral. The phases were separated and the water phase was extracted with chloroform. The chloroform was evaporated and the residue was crystallized from a mixture of acetonitrile and tetrahydrofurane.
Yield: 65%
¹H NMR (CDCl₃): 7.75 (2H, d, J=8 Hz); 8.01 (2H, t, J=8 Hz); 8.05 (1H, t, J=8 Hz); 8.58 (2H, d, J=8 Hz); 8.82 (2H, d, J=8 Hz)
UV ($\lambda_{max}$ in ethanol): 215, 250, 291.

EXAMPLE 10

4'-(4-Nitrophenyl)-6,6''-dicyano-2,2';6',2''-terpyridine, 8b

This compound was synthesized using a method analogous to the synthesis described in Example 9, 8a. The crude product was purified by crystallization from a mixture of acetonitrile and tetrahydrofurane.
Yield: 56%
¹H NMR (DMSO): 8.22 (2H, dd, J=8 Hz and 1 Hz); 8.30 (2H, d, J=9 Hz); 8.33 (2H, t, J=8 Hz); 8.43 (2H, d, J=9 Hz); 8.77 (2H, s); 8.01 (2H, dd, J=8 Hz and 1 Hz).

EXAMPLE 11

4'-(3-Nitrophenyl)-6.6''-dicyano-2,2';6',2''-terpyridine, 8c

This compound was synthesized using a method analogous to the synthesis described in Example 9, 8a. The crude product was purified by crystallization from a mixture of acetonitrile and tetrahydrofurane.
Yield: 71%
¹H NMR (DMSO): 7.90 (1H, t, J=8 Hz); 8.22 (2H, dd, J=8 Hz and 1 Hz); 8.33 (2H, t, J=8 Hz); 8.41–8.45 (1H, m); 8.47–8.72 (1H, m); 8.72 (1H, s); 8.77 (2H, s); 9.00 (2H, d, J=8 Hz).

EXAMPLE 12

6,6''-Bis(aminomethyl)-2,2';6',2''-terpyridine pentahydrochloride, 9a

Compound 8a (0.55 g, 1.9 mmol) was suspended in dry tetrahydrofurane (15 ml). The suspension was bubbled with nitrogen. Borane tetrahydrofurane complex (1M, 25 ml, 25.0 mmol) was slowly added. After stirring overnight, the extra borane was destroyed by adding methanol. The mixture was evaporated to dryness and the residue was dissolved in ethanol (30 ml) saturated with hydrochloric acid. After stirring for one hour the solution was cooled and the product was filtrated.
Yield: 54%
¹H NMR (D₂O): 4.68 (4H, s); 7.89 (2H, d, J=8 Hz); 8.31 (2H, t, J=8 Hz); 8.51 (2H, d, J=8 Hz); 8.82 (2H, d, J=8 Hz); 8.90 (1H, t, J=8 Hz)
UV ($\lambda_{max}$ in H₂O): 232, 293

EXAMPLE 13

4'-(4-Nitrophenyl)-6,6''-bis(aminomethyl)-2,2';6',2''-terpyridine pentahydrochloride, 9b This compound was synthesized using a method analogous to the synthesis described in Example 12, 9a. The product was not purified and therefore no proper NMR data was taken. The crude product was used as such in the next step.
Yield: 56% of crude product

EXAMPLE 14

4'-(3-Nitrophenyl)-6,6''-bis(aminomethyl)-2,2';6',2''-terpyridine pentahydrochloride, 9c This compound was synthesized using a method analogous to the synthesis described in Example 12, 9a. The crude product was used in the next step without further purifications.
Yield: 61% of crude product

EXAMPLE 15

6,6''-Bis[N,N-bis(t-butoxycarbonylmethyl)aminomethyl]-2,2';6',2''-terpyridine, 10a Compound 9a (0.43 g, 0.9 mmol), acetonitrile (15 ml), dry sodium carbonate (2.00 g) and t-butyl ester of bromoacetic acid (1.44 g, 7.4 mmol) was refluxed for two hours and the salts were filtered. The organic phase was evaporated and purified with flash chromatography (silica, chloroform).
Yield: 38%
¹H NMR (CDCl₃): 1.48 (36H, s); 3.56 (8H, s); 4.15 (4H, s); 7.66 (2H, d, J=8 Hz); 7.84 (2H, t, J=8 Hz); 7.90 (1H, t, J=8 Hz); 8.47 (2H, d, J=8 Hz); 8.50 (2H, d, J=8 Hz)
UV ($\lambda_{max}$ in ethanol): 235, 288.

EXAMPLE 16

4'-(4-Aminophenyl)-6,6''-bis[N,N-bis(ethoxycarbonylmethyl)aminomethyl]-2,2';6',2''-terpyridine, 10b The corresponding nitrocompound was synthesized from 9b and an ethyl ester of bromoacetic acid using a method analogous to the synthesis described in 10a. The product was purified with flash chromatography (silica, chloroform with methanol gradient).

Yield: 20%

$^1$H NMR (CDCl$_3$): 1.25 (12H, t, J=7 Hz); 4.18 (8H, q, J=7 Hz); 3.71 (8H, s); 4.23 (4H, s); 7.66 (2H, dd, J=8 Hz and 2 Hz); 7.90 (2H, t, J=8 Hz); 8.06 (2H, d, J=9 Hz); 8.42 (2H, d, J=9 Hz); 8.57 (2H, dd, J=8 Hz and 2 Hz); 8.76 (2H, s).

The aminocompound 10b was synthesized from the corresponding nitrocompound using a method analogous to the synthesis described in 10c.

Yield: 16%

EXAMPLE 17

4'-(3-Aminophenyl)-6,6''-bis[N,N-bis(ethoxycarbonylmethyl)aminomethyl]-2,2';6', 2''-terpyridine, 10c The corresponding nitrocompound was synthesized from 9c and an ethyl ester of bromoacetic acid using a method analogous to the synthesis described in 10a. The product was purified with flash chromatography (silica, chloroform with methanol gradient).

Yield: 53%

$^1$H NMR (CDCl$_3$): 1.24 (12H, t, J=8 Hz); 4.17 (8H, q, J=8 Hz); 3.69 (8H, s); 4.23 (4H, s); 7.67 (2H, dd, J=8 Hz and 2 Hz); 7.89 (2H, t, J=8 Hz); 7.85-8.30 (4 H, m); 8.57 (2H, dd, J=8 Hz and 2 Hz); 8.75 (2H, s).

The aminocompound 10c was synthesized from the corresponding nitrocompound (50 mg, 0.7 mmol) which was dissolved in methanol (2 ml). 10% Palladium on carbon (10 mg) was added followed by slow addition of sodium borohydride (4 mg, 0.1 mmol). After one hour the reaction mixture was filtered and the solution was evaporated. The residue was dissolved in 0.1M sodium hydroxide solution and the product was extracted with chloroform from the water phase. The organic phase was dried and evaporated. The product was purified with flash chromatography (CHCl$_3$, MeOH; 10:0.5).

Yield: 79%

EXAMPLE 18

6,6''-Bis[N,N-bis(carboxymethyl)aminomethyl]-2,2';6',2''-terpyridine, 11a

Tetraester (10a) (260 mg, 0.4 mmol) was dissolved in trifluoroacetic acid (3 ml). After two hours the trifluoroacetic acid was evaporated, some diethyl ether was added and the product was filtered.

Yield: 87%

$^1$H NMR (DMSO): 3.99 (8H, s); 4.47 (4H, s); 7.65 (2H, d, J=8 Hz); 8.10 (2H, t, J=8 Hz); 8.11 (1H, t, J=8 Hz); 8.48 (2H, d, J=8 Hz); 8.61 (2H, d, J=8 Hz)

UV ($\lambda_{max}$ in water): 237, 288, 305.

EXAMPLE 19

4'-(4-Aminophenyl)-6,6''-bis[N,N-bis(carboxymethyl)aminomethyl]-2,2';6',2''-terpyridine, 11b This compound was synthesized using a method analogous to the synthesis described in Example 20, 11c.

Yield: 100%

$^1$H NMR (DMSO): 3.82 (8H, s); 4.31 (4H, s); 6.90 (2H, d, J=7 Hz); 7.67 (2H, d, J=8 Hz); 7.80 (2H, d, J=9 Hz); 8.08 (2H, t, J=8 Hz); 8.60 (2H, d, J=8 Hz); 8.67 (2H, s).

EXAMPLE 20

4'-(3-Aminophenyl)-6,6''-bis[N,N-bis(carboxymethyl)aminomethyl]-2,2';6',2''-terpyridine, 11c The corresponding tetraester, 10c (0.10 g, 0.17 mmol) was dissolved in 5 ml 0.5M KOH-EtOH solution. After 2 hours stirring at room temperature, the ethanol was evaporated to dryness and water was added. The mixture was stirred at room temperature for 30 min whereafter the product was precipitated with 2M hydrochloric acid.

Yield: 100%

$^1$H NMR (DMSO): 3.74 (8H, s); 4.27 (4H, s); 7.71 (2H, d, J=7 Hz); 7.87 (1H, t, J=8 Hz); 8.09 (2H, t, J=7 Hz); 8.33 (1H, d, J=8 Hz); 8.62 (1H, d, J=8 Hz); 8.63 (2H, d, J=7 Hz); 8.79 (2H, s); 8.83 (1H, s).

EXAMPLE 21

1-(2,6-Pyridyldicarbonylmethyl)-bispyridinium iodide, 13

2,6-Diacetylpyridine (8.16 g, 50.0 mmol) and iodide (25.38 g, 100.0 mmol) were heated to reflux in pyridine (125 ml) for 2 hours. The solution was cooled, and the brown crystalline pyridinium salt (13) separated by filtration.

Yield: 87%

EXAMPLE 22

6,6''-Dicarboxy-4,4''-diphenyl-2,2';6',2''-terpyridine, 16a

A solution of 13 (2.86 g, 5.0 mmol), 2-oxo-4-phenyl-3-butenoic acid (1.76 g, 10.0 mmol) and ammonium acetate (8.86 g, 115.0 mmol) in acetic acid (50 ml) was heated to reflux for 5 hours, whereupon the brown solution as cooled. The solid material was filtered and dried in air. The ammonium salt of 2 was dissolved in water and acidified with 6M HCl (pH about 1). The product was filtered and washed with water.

Yield: 34% m.p. 279° C. (dec.).

$^1$H NMR (DMSO): 7.56-8.06 (10H, m); 8.27 (1H, t); 8.40 (2H, d); 8.70 (2H, d); 9.18 (2H, d).

IR (KBr): 1760, 1715, 1695, 1420, 1365, 1272 cm$^{-1}$ (C=O and C—O)

EXAMPLE 23

6,6''-Dicarboxy-4,4''-bis(4-nitrophenyl)-2,2';6',2''-terpyridine, 16b

Compound 16b was synthesized from 13 and 15b using a method analogous to the synthesis described in 16a.

Yield: 57%

$^1$H NMR (DMSO): 8.24 (1H, t); 8.28 (4H, d); 8.37 (4H, d); 8.43 (2H, d); 8.65 (2H, d); 9.13 (2H, d).

EXAMPLE 24

6,6''-Dicarboxy-4,4''-bis(3-nitrophenyl)-2,2';6'2''-terpyridine, 16c

Compound 16c was synthesized from 13 and 15c using a method analogous to the synthesis described in 16a.

Yield: 81%

EXAMPLE 25

6,6''-Bis(methoxycarbonyl)-4,4''-diphenyl-2,2';6'2''-terpyridine, 17a

One drop of concentrated sulfuric acid was added to a suspension of 16a (0.77 g, 1.6 mmol) in methanol (5 ml). The mixture was heated to reflux for 24 hours. The cold mixture was filtered ad the product was crystallized from dichloromethane.

Yield: 61%
m.p. 285.5°–286.5° C.
$^1$H NMR (CDCl$_3$): 4.13 (6H, s); 7.49–7.88 (10H, m); 8.07 (1H, t); 8.44 (2H, d); 8.67 (2H, d); 9.07 (2H, d).
IR (KBr); 1741, 1725, 1255, 1144 cm$^{-1}$ (C=O and C—O).

EXAMPLE 26

6,6''-Bis(methoxycarbonyl)-4,4''-bis(4-nitrophenyl)-2,2';6',2''-terpyridine, 17b Compound 17b was synthesized from 16b using a method analogous to the synthesis described in 17a.
Yield: 45%
$^1$H NMR (CDCl$_3$): 4.05 (6H, s); 7.80–9.03 (15H, m).
IR (KBr): 1740, 1250, 1125 cm$^{-1}$ (C=O and C—O), 1525, 1345 cm$^{-1}$ (NO$_2$).

EXAMPLE 27

6,6''-Bis(methoxycarbonyl)-4,4''-bis(3-nitrophenyl)-2,2';6',2''-terpyridine, 17c Compound 17c was synthesized from 16c using a method analogous to the synthesis described in 17a.
Yield: 38%
$^1$H NMR (CDCl$_3$): 4.05 (3H, s); 4.09 (3H, s); 4.09 (3H, s); 7.75–8.97 (15H, m)
IR (KBr): 1725, 1260, 1130 cm$^{-1}$ (C=O and C—O), 1530, 1340 cm$^{-1}$ (NO$_2$).

EXAMPLE 28

6,6''-Bis(hydroxymethyl)-4,4''-diphenyl-2,2';6',2''-terpyridine, 18a

Sodium borohydride (0.13 g, 3.5 mmol) was added to a suspension of 17a (0.40 g, 0.8 mmol) in absolute ethanol (10 ml). After stirring for 2 hours at room temperature the mixture was heated to reflux for 15 hours. The solution was evaporated in vacuo. A saturated solution of sodium hydrogen carbonate (5 ml) was added to the residue. After the solution was brought to the boil, water (15 ml) was added. The mixture was allowed to stand overnight in the cold. The precipitate was filtered, dried in air and finally crystallized from methanol.

Yield: 47%
m.p. 218°–219° C.
$^1$H NMR (DMSO): 4.75 (4H, s); 7.52–7.95 (10H, m); 7.86 (2H, d); 8.14 (1H, t); 8.49 (2H, d); 8.81 (2H, d).

EXAMPLE 29

6,6''-Bis(hydroxymethyl)-4,4''-bis(4-nitrophenyl)-2,2';6',2''-terpyridine, 18b

Compound 18b was synthesized from 17b using a method analogous to the synthesis described in 18a.
Yield: 40%

EXAMPLE 30

6,6''-Bis(hydroxymethyl)-4,4''-bis(3-nitrophenyl)-2,2';6',2''-terpyridine, 18c

Compound 18c was synthesized from 17c using a method analogous to the synthesis described in 18a.
Yield: 56%
$^1$H NMR (DMSO): 4.98 (4H, s); 7.86–9.13 (15H, m)
IR (KBr): 1530, 1350 cm$^{-1}$ (NO$_2$).

EXAMPLE 31

6,6''-Bis(bromomethyl)-4,4''-diphenyl-2,2';6',2''-terpyridine, 19a

A solution of phosphorous tribromide (0.12 g, 0.4 mmol) in chloroform (1 ml) was added to a solution of 18a (0.13 g, 0.3 mmol) in chloroform (17 ml). The mixture was refluxed for 11 hours whereafter the mixture was neutralized with 5% sodium hydrogen carbonate. The aqueous layer was extracted with chloroform (3×20 ml). The combined organic phase was dried with sodium sulfate and evaporated in vacuo. The residue was crystallized from dichloromethane.

Yield: 29%
m.p. 253.5°–255.5° C.
$^1$H NMR (CDCl$_3$): 4.73 (4H, s); 7.47–7.81 (10H, m); 7.73 (2H, d); 8.01 (1H, t); 8.57 (2H, d); 8.79 (2H, d).

EXAMPLE 32

6,6''-Bis(bromomethyl)-4,4''-bis(4-nitrophenyl)-2,2'; 6',2''-terpyridine, 19b

Compound 19b was synthesized from 18b using a method analogous to the synthesis described in 19a.
Yield: 37%
$_1$H NMR (CDCl$_3$): 4.75 (4H, s); 7.40–8.70 (15H, m).

EXAMPLE 33

6,6''-Bis(bromomethyl)-4,4''-bis(3-nitrophenyl)-2,2';6',2''-terpyridine, 19c

Compound 19c was synthesized from 18c using a method analogous to the synthesis described in 19a.
Yield: 50%
$^1$H NMR (CDCl$_3$): 4.78 (2H, s); 4.83 (2H, s); 7.48–8.65 (15H, m)

EXAMPLE 34

6,6''-Bis[N,N-bis(carboxymethyl)aminomethyl]-4,4''-diphenyl-2,2';6',2''-terpyridine, 20a Potassium carbonate (120 mg, 0.9 mmol) was added to a mixture of 19a (47 mg, 0.08 mmol) and di-t-butyl iminodiacetate (41 mg, 0.20 mmol) in dry acetonitrile (5 ml), and the mixture was stirred for 24 hours at room temperature. The mixture was evaporated in vacuo, the residue was stirred with chloroform (10 ml), washed with water (2×10 ml) and dried with sodium sulfate. Evaporation gave an oil which was characterized by NMR spectrum. The oil was dissolved in trifluoroacetic acid (3 ml) and kept at room temperature for 16 hours. The trifluoroacetic acid was evaporated in vacuo, the solid residue was triturated with ethyl ether.

Yield: 59%
$^1$H NMR (DMSO): 3.71 (8H, s); 4.27 (4H, s); 7.54–7.96 (10H, m); 8-04 (2H, d); 8.18 (1H, t); 8.51 (2H, d); 8.85 (2H, d)
IR (KBr): 1734, 1630, 1395, 1200 cm$^{-1}$ (C=O and C—O).

EXAMPLE 35

6,6''-Bis[N,N-bis(carboxymethyl)-aminomethyl]-4,4''-bis(4-aminophenyl)-2,2';6',2''-terpyridine, 20b The reaction between 19b (0.11 g, 0.2 mmol) and diethyl iminodiacetate (76 mg, 0.40 mmol) in dry acetonitrile (10 ml) and potassium carbonate (0.27 g, 20 mmol) was made in analogy with 20a. The reaction gave an oil which was purified with flash chromatography (silica, MeOH/CHCl$_3$ 1/19). The oil was dissolved in methanol (5 ml). 10% Palladium on carbon (20 mg) was added followed by slow addition of sodium borohydride (23 mg, 0.60 mmol). After one hour the mixture was filtered and the filtrate was evaporated in vacuo. The residue was dissolved in 0.5M potassium hydroxide ethanol (20 ml). After stirring for 3 hours at room temperature the mixture was evaporated and water (20 ml) was added. The mixture was acidified with 6M HCl (pH about 2.0). The product was filtered and washed with water.

Yield: 60%

$^1$H NMR (DMSO): 3.71 (8H, s); 4.30 (4H, s); 7.75-8.80 (15H, m)

IR (KBr): 1735, 1630, 1400, 1200 cm$^{-1}$ (C=O and C—O).

EXAMPLE 36

6,6''-Bis[N,N-bis(carboxymethyl)-aminomethyl]-4,4''-bis(3-aminophenyl)-2,2';6',2''-terpyridine, 20c Compound 20c was synthesized from 19c using a method analogous to the synthesis described in 20b.

Yield: 79%

$^1$H NMR (DMSO): 3.68 (8H, s); 4.21 (4H, s); 7.63-8.64 (15H, m)

IR (KBr): 1725, 1630, 1400, 1190 cm$^{-1}$ (C=O and C—O).

EXAMPLE 37

L-Lysine ethyl ester (starting compound, Scheme 3)

Thionyl chloride (5.0 ml, 8.06 g, 68 mmol) was added dropwise to 500 ml of ice- cooled dry ethanol. The stirred mixture was kept for 20 min at this temperature and L-lysine hydrochloride (20 g, 109 mmol) was added.

The mixture was then refluxed for 3 h and concentrated to a volume of about 200 ml. 200 ml of diethylether was added and the crystallized product filtered off.

Yield: 29 g (97%)-dihydrochloride. Rf=0.20 (System F)

EXAMPLE 38

ω-N-(4-Nitrobenzoyl)-L-lysine ethyl ester (37)

L-lysine HCl (5 g, 27.4 mmol) dissolved in 50 ml of water was titrated with 5M NaOH to pH 10.5. 4-Nitrobenzoyl chloride (6.6 g, 36 mmol) in dioxane (50 ml) and 5M NaOH were slowly added keeping the vigorously stirred reaction mixture at pH 10.5.

After complete addition and disappearance of the pink colour the reaction mixture was acidified with conc. HCl to pH 2 and extracted four times with diethylether. The aqueous phase was concentrated to dryness, coevaporated twice with 200 ml of dry ethanol and suspended in 250 ml of dry ethanol previously treated with 10 ml of thionyl chloride. The mixture was refluxed for 3 h, filtered and evaporated. The residual material was partitioned between saturated sodium bicarbonate and chloroform/ethanol 1:1 and the organic phase was dried over magnesium sulfate yielding a crude product which was purified by flash chromatography using 5% EtOH/chloroform as eluent.

Yield: 1.08 g (12%) oil crystallizing on standing Rf=0.23 (System A)

H$^1$NMR (60 MHz, CDCl$_3$): 8.25 (d,2H, J=9 Hz), 7.93 (d, 2H, J=9 Hz), 6.87 (s, broad, 1H), 3.99-4.34 (q, 2H), 3.30-3.60 (m, 3H), 1.40-1.75 (m, 8H), 1.11-1.37 (t, 3H)

EXAMPLE 39

α-N-(Methoxycarbonylmethyl)-ω-N-(4-nitrobenzoyl)-L-lysine ethyl ester (38)

Compound (37) (0.54 g, 1.7 mmol) was coevaporated with toluene, dissolved in dry acetonitrile (10 ml) and bromoacetic acid methylester (0.265 g, 1.7 mmol) was added followed by pulverized dry sodium carbonate (2.0 g). The mixture was refluxed for 3 h.

Filtration of the inorganic salts and evaporation of the acetonitrile gave an oily crude product which was purified by flash chromatography.

Yield=0.45 g (68%) oil Rf=0.26 (System A)

H$^1$NMR (60 MHz, CDCl$_3$): 8.25 (d, 2H, J=9 Hz), 7.93 (d, 2H, J=9 Hz), 6.63 (s, broad, 1H), 3.95-4.30 (q, 2H), 3.68 (s, 3H), 3.30-3.60 (m, SH), 1.40-1.75 (m, 7H), 1.11-1.37 (t, 3H).

EXAMPLE 40

ω-N-Monomethoxytrityl-L-lysine ethyl ester (39)

Dry triethylamine (1.8 ml, 18 mmol) was added to a suspension of the starting compound (scheme 3) (1.5 g, 6 mmol) in 20 ml of dry pyridine. To this mixture stirred at RT, solid monomethoxytrityl chloride (1.96 g, 6 mmol) (MMTrCl) was added in small portions during a period of 1 h whereupon the mixture was stirred for additional 2 h. A standard sodium bicarbonate work-up, followed by extraction with chloroform, yielded a crude product contaminated with α-MMTr isomer.

The pure title product was easily isolated by flash column chromatography due to the large Rf difference between the isomers.

Yield: 1.35 g (48%) oil Rf=0.43 (System A)

H$^1$NMR (400 MHz, CDCl$_3$): 7.5-6.75 (m, 14H), 4.18-4.13 (q, 2H), 3.78 (s, 3H), 3.45-3.37 (m, 1H), 2.14-2.10 (t, 2H, J=7 Hz), 1.75-1.35 (m, 9H), 1.26 (t, 3H)

EXAMPLE 41

α-N-(Methoxycarbonylmethyl)-ω-N-monomethoxytrityl-L-lysine ethyl ester (40)

A partially protected L-lysine derivative (39) (1.0 g, 2.13 mmol) was converted to product (40) using the method described in Example 36.

Yield: 0.81 g (70%) oil Rf=0.73 (System A)

H$^1$NMR (400 MHz, CDCl$_3$): 7.46-6.77 (m, 14H), 4.19-4.14 (q, 2H), 3.77 (s, 3H), 3.70 (s, 3H), 3.31-3.45 (q, 2H), 3.22-3.25 (t, 1H), 2.09-2.12 (t, 2H), 1.35-1.70 (m, 6H), 1.23-1.27 (t, 3H)

EXAMPLE 42

ω-N-Trifluoroacetyl-L-lysine ethyl ester (41)

The starting compound (scheme 3) (2.0 g, 8.1 mmol) dissolved in 10 ml of dry ethanol was treated with dry triethylamine (4.09 g, 40.4 mmol). Ethyl trifluoroacetate (1.5 g, 10.5 mmol) was added to the stirred suspension formed, and the mixture was refluxed for 6 h.

All volatiles were then evaporated and the residue was partitioned between saturated sodium hydrogen carbonate and chloroform/ethanol 1:1.

The combined organic phase (5×60 ml) was evaporated, coevaporated with toluene and flash chromatographed to give the title product in the form of a colorless oil.

Yield: 1.9 g (87%) Rf=0.72 (System D)

$H^1$NMR (400 MHz, $CDCl_3$): 7.10 (t, 1H, exchangeable), 4.21–4.16 (q, 2H), 3.45–3.40 (m, 1H), 3.38–3.31 (m, 2H), 1.84 (s, 2H, exchangeable), 1.82–1.40 (m, 6H), 1.28 (t, 3H).

EXAMPLE 43

α-N-(Methoxycarbonylmethyl)-ω-N-trifluoroacetyl-L-lysine ethyl ester (42)

L-lysine derivative (41) (1.0 g, 3.7 mmol) was converted to the product (42) by means of a method analogous to Example 36.

Yield: 1.05 g (83%) oil Rf=0.48 (System A)

$H^1$NMR (60 HMz, $CDCl_3+CD_3OD$): 4.4–4.0 (q, 2H), 3.68 (s, 3H), 3.5–3.1 (m, 5H), 1.8–1.4 (m, 6H), 1.23 (t, 3H).

EXAMPLE 44

ω-N-(4-Hydroxybutyryl)-L-lysine ethyl ester (43)

L-lysine etyl ester×2 NCl (36) (2 g, 8.1 mmol) in 30 ml of dry ethanol was treated with dry triethylamine (5.63 ml, 40.5 mmol) and γ-butyrolactone (0.7 g, 8.1 mmol) and the resultant suspension was refluxed for 3 h.

Evaporation of volatiles and coevaporation with toluene yielded a crude product which was purified by flash chromatography using 20% methanol/chloroform as solvent.

Yield: 1.54 g (73%) oil Rf=0.28 (System D)

1 $H^1$NMR (400 MHz, $CDCl_3+CD_3OD$): 4.30–4.22 (q, 2H), 3.72–3.77 (m, 1H), 3.58–3.65 (t, 2H), 3.18–3.28 (m, 2H), 2.30–2.36 (t, 2H), 1.40–2.00 (m, 8H), 1.28–1.34 (t, 3H).

EXAMPLE 46

Fluorescence of europium and terbium chelates of compound 20a

The relative fluorescence yield $\phi_{rel}$ of the europium and terbium chelates of compound 20a were measured in equimolar $10^{-5}$M solutions of compound 20a and the corresponding lanthanide ion. Fluorescence measurements were done on a Perkin-Elmer LS-5 ® spectrofluorometer using the phosphorescence mode which allowed the decay curves of the lanthanide fluorescence to be measured. The fluorescence yield is reported relative to the fluorescence of the uncomplexed lanthanide cation (Ln) using the equation:

$$\phi_{rel} = \frac{I_{che}C_{Ln}k_{Ln}}{I_{Ln}C_{che}k_{che}}$$

where $I_{che}$ and $I_{Ln}$ are the preexponential terms of the emission decay curves for the chelated and uncomplexed lanthanide cation, respectively (614 nm for europium and 544 nm for terbium). The excitation wavelength for the uncomplexed europium was 395 nm and for terbium 370 nm. $C_{Ln}$ and $C_{che}$ are the concentrations of free and complexed lanthanide cation, respectively, and $k_{Ln}$ and $k_{che}$ the corresponding decay constants. For compound 20a the relative fluorescence yield for the europium complex becomes $2.1\times10^6$ and for the terbium complex $8.1\times10^4$. The excitation wavelength for the chelates was in both cases 340 nm.

We claim:

1. A lanthanide chelate in which a lanthanide selected from the group consisting of $Eu^{3+}$, $Tb^{3+}$, $Sm^{3+}$ and $Dy^{3+}$ is chelated to a terpyridine compound having the structure

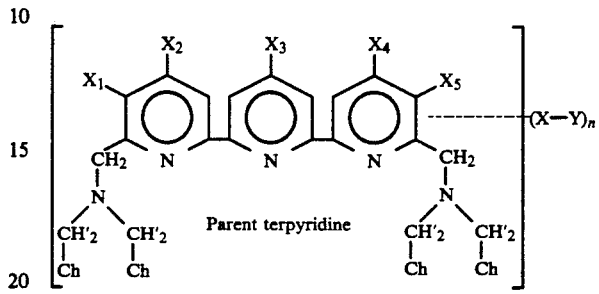

wherein
- (i) n=1 or 2,
- (ii) $X_1=X_5$ hydrogen,
- (iii) $X_2$, $X_3$ and $X_4$ are selected from the group consisting of hydrogen, hydroxy, amino, amido, alkoxy, alkyl, alkynyl, aryl, aralkyl, aryloxy, arylamino and arylethynyl, with the proviso that alkyl has less than 12 carbon atoms and aryl is selected from phenyl, quinolyl, naphthyl, pyridyl and pyrimidyl,
- (iv) Ch is a chelating group selected from —$COO^-$, —$OPO_3^{2-}$ and- $PO_3^{2-}$,
- (v) X-Y is a substituent replacing a group $X_1$-$X_5$ or H', in which X is a bridge hot participating in the chelating and consisting of a pure hydrocarbon chain of 1-12 carbon atoms and at least one structural element selected from the group consisting of secondary and tertiary amines, aliphatic disulfides, aliphatic thioethers, ethers, esters and diaza, and
Y is a residue of a compound selected from the group consisting of antigens, haptens, antibodies and nucleic acids, said residue retaining the biospecific affinity of said compound.

2. A chelate according to claim 1 wherein the pure hydrocarbon chain is selected from the group consisting of phenyl and naphthyl.

3. A chelate according to claim 1 wherein n=1; $X_2$ and $X_4$ are hydrogens; Ch is —$COO^-$; X-Y is 4-aminophenyl to which the residue Y is linked at the 4-amino group; and X-Y replaces $X_3$.

4. A chelate according to claim 1 wherein n=1; $X_2$ and $X_4$ are hydrogens; Ch is —$COO^-$; X-Y is 3-aminophenyl to which the residue Y is linked at the 3-amino group; and X-Y replaces $X_3$.

5. A chelate according to claim 1 wherein n=2; $X_3$ is hydrogen; Ch is —$COO^-$; X-Y is 4-aminophenyl to which the residue Y is linked at the 4-amino group; and X-Y replaces $X_2$ and $X_4$, respectively.

6. A chelate according to claim 2 wherein n=2; $X_3$ is hydrogen; Ch is —$COO^-$; X-Y is 3-aminophenyl to which the residue Y is linked at the 3-amino group; and X-Y replaces $X_2$ and $X_4$, respectively.

7. A chelate according to claim 2 wherein n=1; $X_2$ and $X_4$ are hydrogens; X-Y is isothiocyanatophenyl to which the residue Y is linked at the isothiocyanato group; and X-Y replaces $X_3$.

* * * * *